(12) United States Patent
Jang

(10) Patent No.: US 6,948,875 B1
(45) Date of Patent: Sep. 27, 2005

(54) TOOTH BRUSH DEVICE

(75) Inventor: Hyo Sol Jang, 42 San, Yongdoo-dong, Dukyang-gu, Koyang city, Gyunggi-do (KR)

(73) Assignees: Ryan Kyung Soo Choi, St. Joseph, MI (US); Hyo Sol Jang, Koyang (KR)

( * ) Notice: Subject to any disclaimer, the term of this patent is extended or adjusted under 35 U.S.C. 154(b) by 0 days.

(21) Appl. No.: 11/075,730

(22) Filed: Mar. 10, 2005

(30) Foreign Application Priority Data

Aug. 16, 2004 (KR) ..................... 10-2004-0064407

(51) Int. Cl.[7] .............................................. B43K 5/02

(52) U.S. Cl. ................... 401/146; 401/149; 401/150; 401/180; 401/188 R; 401/278; 401/279

(58) Field of Search ............................... 401/146, 149, 401/150, 176, 180, 187, 188 R, 270, 278, 401/279

(56) References Cited

U.S. PATENT DOCUMENTS

| | | | | |
|---|---|---|---|---|
| 4,236,651 A | * | 12/1980 | Meyer et al. | 401/270 |
| 5,158,383 A | * | 10/1992 | Glover et al. | 401/150 |
| 5,393,153 A | * | 2/1995 | Bouthillier et al. | 401/146 |
| 6,039,489 A | * | 3/2000 | Harman et al. | 401/146 |

* cited by examiner

*Primary Examiner*—Tuan Nguyen
(74) *Attorney, Agent, or Firm*—Mayer, Brown, Rowe & Maw LLP

(57) ABSTRACT

A toothbrush device is provided, which includes a brush, a toothpaste storing case, and a push-button pump disposed between the brush and the toothpaste storing case; a first check valve disposed between the toothpaste storing case and the pump, a second check valve disposed between the first check valve and the toothpaste storing case, and a first spring disposed between the first and second check valves; wherein the first check valve includes a second spring and a piston in sequence in a direction away from the pump, and has a working element which includes a rod with movement grooves at a first end thereof and a securing part at a second end thereof.

17 Claims, 4 Drawing Sheets

TOOTH BRUSH DEVICE

BACKGROUND OF THE INVENTION

1. Field of the Invention

The present invention relates to a toothbrush device provided with toothpaste, and more particularly to a toothbrush device in which a toothpaste storing case is mounted at one end of the toothbrush, and the toothpaste is supplied to a brush from the toothpaste storing case by a pumping element, thereby promoting convenience of use and reducing waste.

2. Discussion of the Background

In general, people brush their teeth with a toothbrush in the morning and after eating food, and a toothbrush and toothpaste are required. When someone brushes their teeth, a toothbrush having a brush and toothpaste together in one unit is becoming more popular. The toothpaste is desirably provided to the brush, and the toothpaste may be evenly spread on the teeth.

Therefore, toothbrush and toothpaste are always required for brushing and, for convenience at school or office or when taking a trip, having the brush and paste together in a single unit is desirable.

The present applicant has suggested a toothbrush that is convenient to carry and use under Korean Utility Model No. 225530 (application No. 20-1999-0001654, filing date 1999.02.04), wherein a toothpaste case is integrally coupled with a toothbrush and toothpaste in the toothpaste case is supplied to the toothbrush by pumping operation.

This toothbrush, however, has a problem in that the toothpaste is supplied to the toothbrush too slowly and incorrectly since a pumping element employs a check valve using a ball. The toothpaste is not supplied to a front part of the brush sufficiently or in an amount desired by a user. Furthermore, the toothpaste is apt to flow down along the toothbrush, so that the use of the toothbrush is not convenient and waste of the toothpaste results.

Rivin et al. in U.S. Pat. No. 6,142,694 discloses a toothbrush with a storage for toothpaste. Rivin's toothbrush has a rotatable spindle mounted inside the storage compartment near the neck section, a grippable dial situated outside the storage compartment, by means of which the spindle may be rotated, a length of cord fixed and wound on the spindle, and a piston connected to the cord. When the grippable dial and spindle are rotated, the piston moves forward by the pulling action of the connecting cord, thereby forcing toothpaste from the storage compartment into the conduit and out to the head portion and bristles.

Although this disclosure offers the convenience of operation using one hand, it is not convenient enough for some users. According to Rivin et al., using the grippable dial implies that a user should watch the brush section or the rotation angle of the dial to supply a certain quantity of toothpaste to the brush. This is inconvenient because some people use a toothbrush before wearing glasses/contact lenses or after taking glasses/contact lenses off.

In other conventional toothbrushes, a brush is mounted in a front end of a toothbrush in an assembling structure, and a supply hose is provided in an inner path to be connected to a pump, wherein an end of the supply hose is positioned in the brush so that toothpaste is supplied to the front part rather than the center of the brush via the supply hose by the pump. Therefore, the toothpaste transfers via the supply hose, and the transfer of the toothpaste is not smooth. Particularly, the user must transfer the toothpaste to the brush. Further, the toothpaste flows down from the toothbrush while using, thereby causing the waste of the toothpaste.

In another conventional toothbrush device, the grippable dial is provided so that toothpaste is transferred from the storage compartment into a path and out to its head portion and brush. Therefore, a user must watch the brush section or the rotation angle of the dial to supply a certain quantity of toothpaste to the brush.

SUMMARY OF THE INVENTION

The problems mentioned above, and others, are solved by the present invention, which is generally directed to a toothbrush device having a toothpaste storing case.

One object of the present invention is to provide a toothbrush device having a toothpaste case, in which toothpaste is easily supplied in suitable amount to the brush.

One object of the present invention is to provide a toothbrush device having a toothpaste case, in which toothpaste is precisely and sufficiently pumped to a front part of a toothbrush for a user to effectively brush his teeth.

Accordingly, one embodiment of the present invention provides a toothbrush device, which includes:

a brush, a toothpaste storing case, and a push-button pump disposed between the brush and the toothpaste storing case;

a first check valve disposed between the toothpaste storing case and the pump, a second check valve disposed between the first check valve and the toothpaste storing case, and a first spring disposed between the first and second check valves;

wherein the first check valve includes a second spring and a piston in sequence in a direction away from the pump, and has a working element which includes a rod with movement grooves at a first end thereof and a securing part at a second end thereof;

wherein the second check valve includes a fixing element having a fitting part disposed about a central axis at a first end thereof, a securing part disposed at a second end and about an outer periphery thereof, and a rubber plate disposed between the securing part and the toothpaste storing case; and wherein the first spring is in contact with the securing part of the first check valve and the securing part of the second check valve.

Another embodiment of the present invention provides a method, which includes contacting the above toothbrush device with toothpaste.

Another embodiment of the present invention relates to a method, which includes brushing a subject's teeth with the above toothbrush device.

BRIEF DESCRIPTION OF THE ATTACHED DRAWINGS

The invention will be described in detail with reference to the following drawings in which like reference numerals refer to like elements wherein.

DETAILED DESCRIPTION OF THE PREFERRED EMBODIMENTS

Reference will now be made in detail to the preferred embodiments of the present invention, examples of which are illustrated in the accompanying drawings, and which are not limiting unless otherwise specified.

One preferred embodiment of the present invention relates to a toothbrush device including a toothbrush part having a brush at a front part, a toothpaste storing case at a rear part connected to the brush, and a pump mounted between the brush and the toothpaste storing case for supplying the toothpaste to the brush, includes a path of which a first end is connected to a connection hole of a push button connected to the pump, and a second end is formed in the toothbrush so as to be connected to a central inside of the brush, a connection tube connecting the first end of the path to the connection hole of the push button, and formed with a protrusion part on an outer periphery of an end, wherein the protrusion part closely contacts an inner surface of the connection tube, a first check valve coupled with an end of a pipe positioned in the pump together with a spring and a piston in sequence, and having a working element formed with a rod provided with movement grooves at a side and a securing part at the other side, so that the rod is fitted in the pipe via the piston to open or close the movement grooves of the rod in association with the operation of the piston, a second check valve having a fixing element formed with a fitting part in the center, a securing part along an outer periphery of the fitting part, and a rubber plate fitted in the center of the fitting part, wherein the fixing element and the rubber plate are mounted in a suction hole of the pump so that the suction hole of the pump is opened or closed by the rubber plate, and a spring mounted between the securing part formed to the working element of the first check valve and the securing part of the fixing element of the second check valve.

The toothpaste is effectively pumped from the toothpaste case mounted at a side of the toothbrush and precisely and sufficiently supplied to the center of brush. According to the present invention as above, the inconvenience caused by the flowing down of the toothpaste or the waste of the toothpaste may be effectively resolved.

A preferred toothbrush device according to the present invention will be described with reference to FIG. 1 to FIG. 5 in detail.

Figure 1:
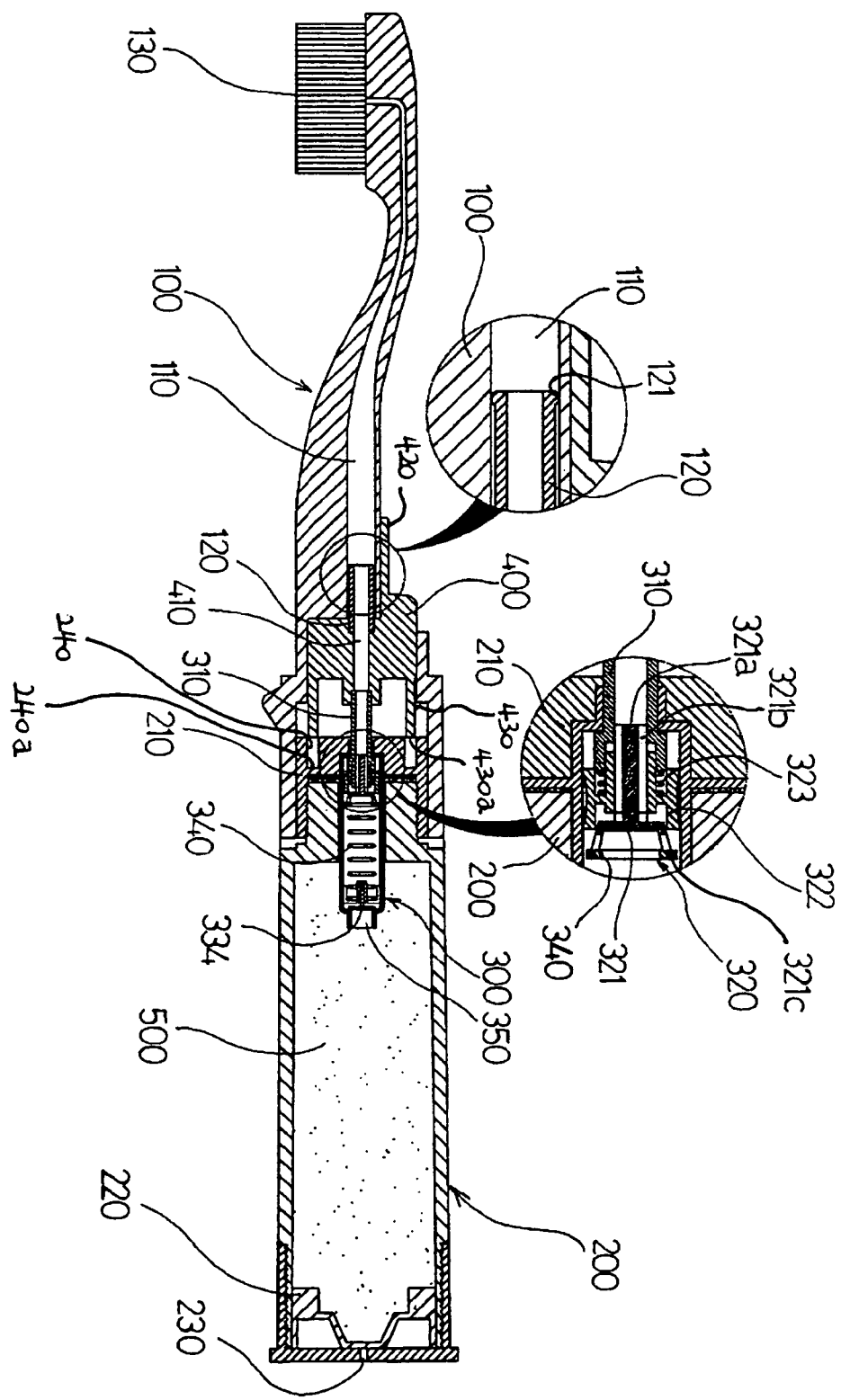
FIG. 1 is a cross-sectional view showing principal parts of a toothbrush device according to one embodiment of the present invention.
Figure 2:
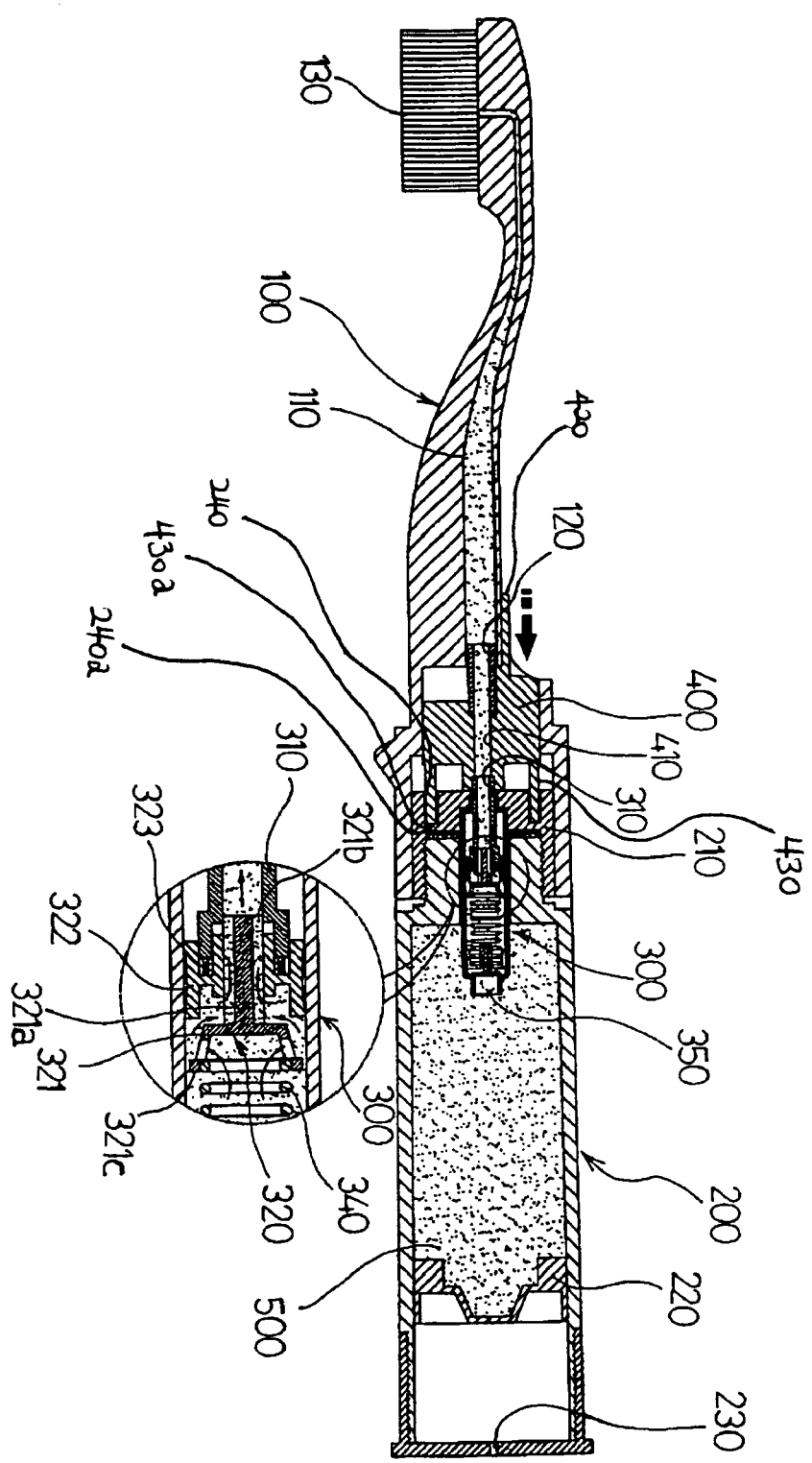
FIG. 2 is a cross-sectional view showing operations of the principal parts of a toothbrush device according to one embodiment of the present invention.
Figure 3:
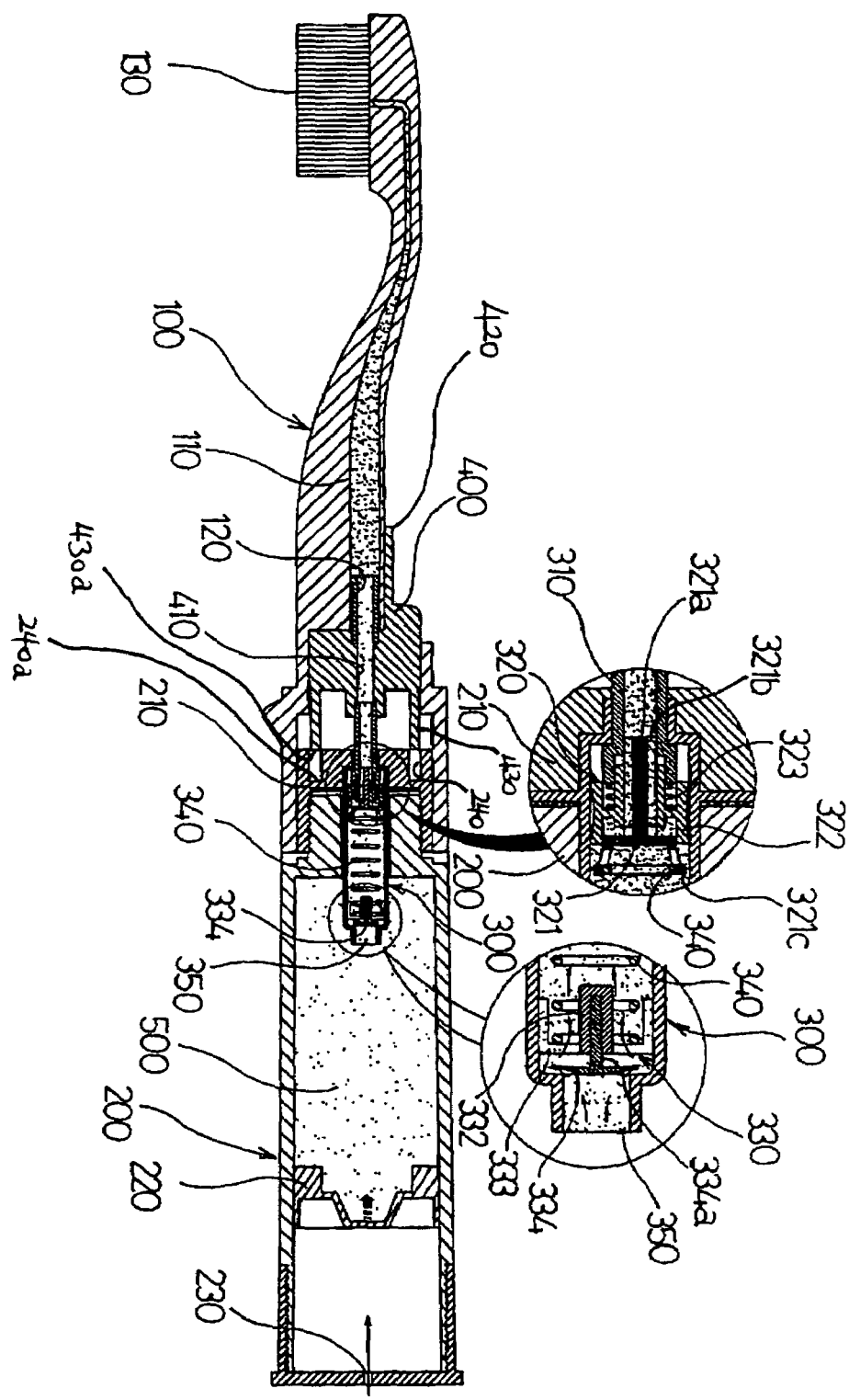
FIG. 3 is a cross-sectional view showing operations of the principal parts of a toothbrush device according to another embodiment of the present invention.
Figure 4:
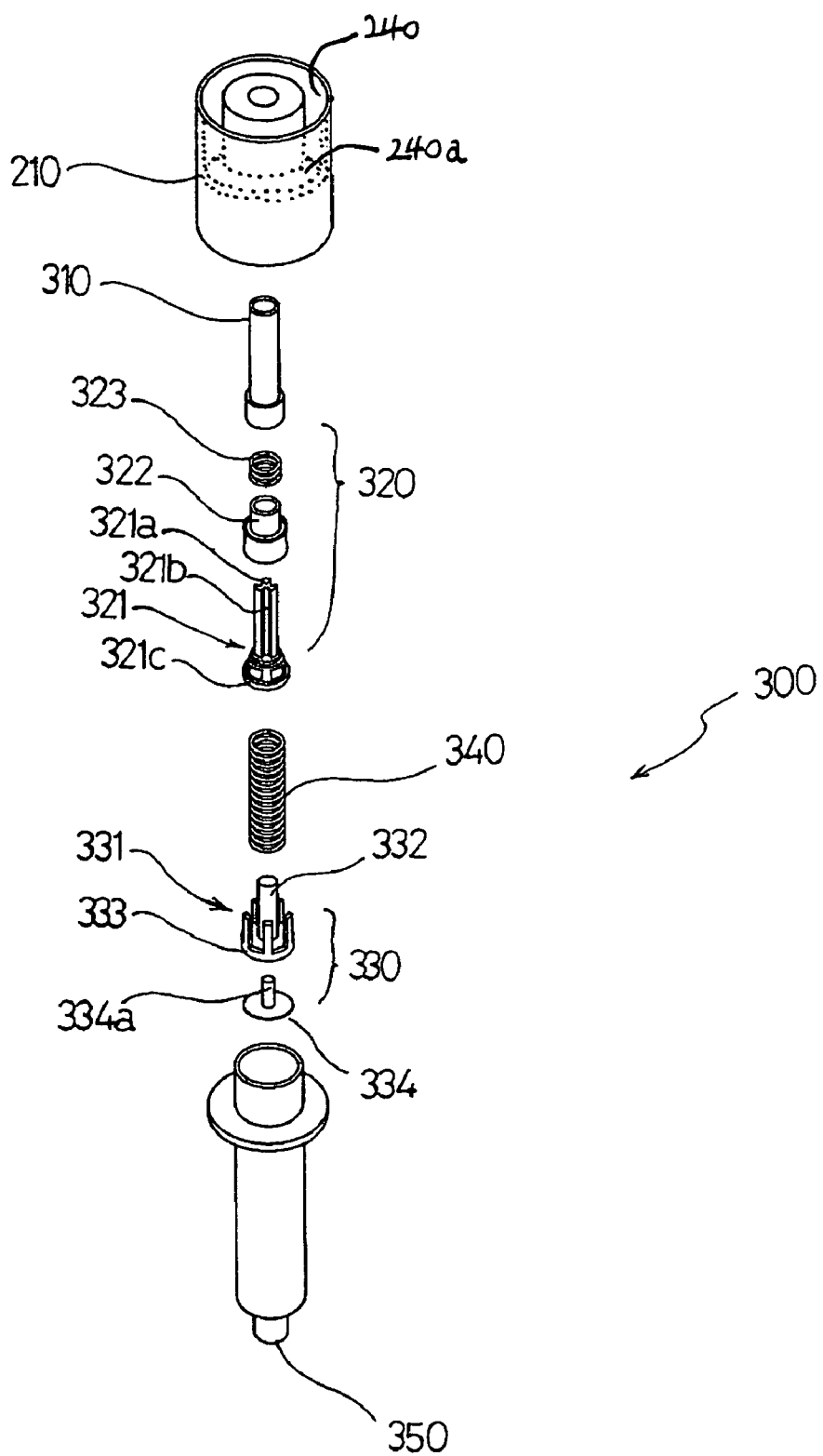
FIG. 4 is a cross-sectional view showing pump structure of a toothbrush device according to one embodiment of the present invention.

FIG. 1 is a cross-sectional view showing principal parts of a toothbrush device according to the present invention. FIG. 2 is a cross-sectional view showing operations of the principal parts of a toothbrush device according to a preferred embodiment of the present invention. FIG. 3 is a cross-sectional view showing operations of the principal parts of a toothbrush device according to another preferred embodiment of the present invention. FIG. 4 is a cross-sectional view showing pump structure of a toothbrush device according to the present invention.

One preferred embodiment of the present toothbrush device has a toothbrush part 100 having a brush 130 at a front part, and a toothpaste storing case 500 at a rear part connected to the brush and having toothpaste 200, for supplying the toothpaste 500 to the brush 130 of the toothbrush part 100 by the operation of a pump 300. A path 110 has a first end connected to a connection hole 410 of a push button 400 connected to the pump 300, and a second end formed in the toothbrush part 100 so as to be connected to a central inside part of the brush 130, and a connection tube 120 connects the first end of the path 110 to the connection hole 410 of the push button 400, and has a protrusion part 121 in the shape of O-ring on an outer periphery of an end, wherein the protrusion part 121 closely contacts an inner surface of the connection tube 120.

A first check valve 320 is coupled with an end of a pipe 310 positioned in the pump 300 together with a spring 323 and a piston 322 in sequence, and has a working element 321 formed with a rod 321a provided with movement grooves 321b at a side and a securing part 321c at the other side, so that the rod 321a fits in the pipe 310 via the piston 322 to open or close the movement grooves 321b of the rod 321a in association with the operation of the piston 322.

A second check valve 330 has a fixing element 331 formed with a fitting part 332 in the center, a securing part 333 along an outer periphery of the fitting part 332, and a rubber plate 334 fitted in the center of the fitting part 332. The fixing element 331 and the rubber plate 334 are mounted in a suction hole 350 of the pump 300 so that the suction hole 350 of the pump 300 is opened or closed by the rubber plate 334.

A spring 340 is mounted between the securing part 321c formed to the working element 321 of the first check valve 320 and the securing part 333 of the fixing element 331 of the second check valve 330.

In the drawings, reference symbol 220 represents a piston mounted in the toothpaste storing case 200, reference symbol 200 represents an air hole formed at a rear part of the toothpaste storing case, and reference symbol 210 represents a cap mounted at a front part of the toothpaste storing case.

The push button 400 is mounted between the brush 130 and the pump 300. The brush button 400 has a pushing part 420 and a first projection 430, whichis formed to cylindrical shape and has a toe 430a.

The cap 210 mounted between the push button 400 and the toothpaste storing case 200. The cap 210 has a second cavity 240, which is formed to cylindrical shape. The cavity 240 has a bottom 240a and is corresponding to the first projection 430 of the push button 400 so that push button 400 is shuttled at constant length of stroke by the toe 430 meeting the bottom 240a.

In one preferred embodiment of the present invention, the toothpaste storing case 200 receiving the toothpaste 500 is connected to a side of the toothbrush part 100 and the toothpaste 500 received in the toothpaste storing case 200 is supplied to an end of the toothbrush part 100 by the pump 300. The first and second check valves 320, 330 mounted in the pump 300 effectively prevent the backflow of the toothpaste 500 and precisely and speedily transfer the toothpaste 500 to the brush 130 of the toothbrush part 100. Further, the toothbrush device may desirably prevent the inconvenience of use and the waste of the toothpaste caused by the flowing down of the toothpaste when the toothpaste 500 is supplied to the center of the brush 130 of the toothbrush part 100.

Further, since push button 400 is shuttled at constant length of stroke, a certain amount of toothpaste 500 is discharged to the connection hole 410 by one operation (pushing). The toothbrush device may prevent the inconvenience of watching discharged toothpaste or an operation dial.

FIG. 1 illustrates the toothbrush device in accordance with one preferred embodiment of the present invention. In FIG. 1, the brush 130 is provided at the front part of the toothbrush part 100, and the toothpaste storing case 200 receiving the toothpaste 500 is provided at a rear part. The push button 400 and the pump 300 are mounted between the toothbrush part 100 and the toothpaste storing case 200, so that the toothpaste 500 in the toothpaste storing case 200 is supplied to the brush 130 of the toothbrush part 100 by the operation of the pump 300 in association with the operation of the push button 400.

One preferred embodiment of the toothbrush device of the present invention is characterized in that the path 110 is formed in the toothbrush part 100 for transferring the toothpaste 500, the connection tube 120 connects the path 110 of the toothbrush part 100, and the pump 300 is mounted with the first and second check valves 320, 330.

The end of the toothbrush part 100 is not in the separate structure but in the integral structure, the path 110 formed in the toothbrush part 100 is connected to the pump 300 at a side and to the center of the brush 130 mounted to an end of the toothbrush part 100 at the other side. Therefore, the toothpaste 500 is pumped by the pump 300 to be supplied to the top of the center of the brush 130 from the inside of the center of the brush 130 along the path 110 of the toothbrush part 100.

Therefore, according to a preferred embodiment of the present invention, the end of the toothbrush part 100 is not in the separate structure but in the integral structure, and the path 110 is used without the supply hose, so that the structure and the manufacture of the toothbrush device may be simplified. In the above structure, the toothpaste 500 passing through the path 110 is smoothly supplied to the brush 130. Further, the toothpaste 500 is supplied to the center of the brush 130 of the toothbrush part 100, so that the unnecessary waste or flowing down of the toothpaste 500 may be prevented, making toothbrushing more effective.

According to the present invention, push button 400 is desirably shuttled at constant length of stroke and a certain amount of toothpaste 500 is discharged to the connection hole 410 by one operation (pushing). A user may easily supply a certain quantity of toothpaste to the brush only by counting the number of operation (pushing).

The pipe 310 connected to the pump 300 has an end connected to a side of the connection hole 410 of the push button 400 and the other end connected to the path 110 of the toothbrush part 100, wherein the other side of the connection hole 410 and the path of the toothbrush part 100 are connected to each other by the connection tube 120. An end of the connection tube 120 facing the path protrudes as the protrusion part 121 in the shape of O-ring. The connection tube 120 and the path 110 are sealed by the protrusion part 121, so that the toothpaste 500 pumped and transferred to the path 110 of the toothbrush part 100 by the pump 300 is prevented from leaking around the connection part between the toothbrush part 100 and the push button 400.

The first check valve 320 is mounted on the pump 300 for preventing the transferring of the toothpaste 500 to the path 110 of the toothbrush part 100 by the pump 300 regardless of the operation of the push button 400. In the structure of the first check valve 320, an end is connected to the pipe 320 connected to the connection hole 410 of the push button 400 at a side, and mounted with the spring 323 and the piston 322 at the other side. Therefore, the piston 322 lifts or lowers elastically by the spring 323. The working element 321 is provided in the piston 322, wherein the working element 321 is provided at a side with the rod 321a formed with the movement grooves 321b in the triangular directions, and the securing part 321c at the other side.

The rod 321a of the working element 321 is fitted into the piston 322 and connected to the inside of the pipe 310 through the piston 322. The connection part between the rod 321a and the securing part 321c closely contacts a lower end of the piston 322, so that the toothpaste 500 in the pump 300 is prevented from transferring to the movement grooves 321b of the rod 321a by the piston 322.

As the push button 400 is pressed, the pipe 310 lowers in the pump 300 by the push button 400, wherein the piston 322 mounted to the pipe 310 compresses the spring 323 and lifts toward the pipe 310 while closely contacting an inner peripheral surface of the pump 300. If the piston 322 lifts toward the pipe 310 as above, the lower end of the piston 322 is separated from the connection part between the rod 321a and the securing part 321c of the working element 321. Then the toothpaste 500 of the pump 300 transfers along the movement grooves 321b of the rod 321a, passes the pipe 310, the connection hole 410 of the push button 400, the path 110 of the toothpaste part 100 in sequence. The toothpaste is supplied to the brush 130 of the toothbrush part 100 finally.

The second check valve 330 is mounted to a lower part of the pump 300 for preventing the toothpaste 500 transferred to the pump 300 from flowing back to the toothpaste storing case 200. The second check valve 330 has the fixing element 331 formed with the fitting part 332 and the securing part 333, and the rubber plate 334 of which the center part 334a is fitted into the fitting part 332 of the fixing element 331. The rubber plate 334 is positioned at the lower part of the suction hole 350 in the pump 300, blocking the suction hole 350 of the pump 300. The spring 340 is mounted between the securing part 333 of the fixing element 331 of the second check valve 330 and the securing part 321c of the working element 321 of the first check valve 320.

Therefore, in the normal case or when the push button 400 is pressed, the pipe 310, the piston 322 and the first check valve 320 lower and compress the spring 340. Then, the rubber plate 334 blocking the suction hole 350 of the pump 300 prevents the toothpaste 500 in the pump 300 from transferring to the toothpaste storing case 200.

As the push button 400 is released from the pressed state, the spring 340 mounted and compressed between the securing part 333 of the fixing element 331 and the securing part 321c of the working element 321 is restored to an initial state, and the pipe 310, the piston 322 and the first check valve 320 lift in association with the recovery of the spring. Therefore, the toothpaste 500 in the toothpaste storing case 200 transfers to the suction hole 350 of the pump 300 by instant negative force generated by the lifting of the pipe 310, the piston 322, and the first check valve 320. At this time, an outer periphery of the rubber plate 334 of the second check valve 330 is turned and the toothpaste 500 enters into the pump 300 and filled in the pump 300.

When the toothpaste 500 received in the toothpaste case 200 is partially discharged to the outside of the toothbrush part 100 by the pump 300, a space corresponding to the discharged toothpaste is formed. Then, the piston 220 contacts the space at a side and the atmospheric air introduced via the air hole 230 at the other side, wherein the air hole 230 is formed at the rear part of the toothpaste storing case 200.

Therefore, the piston 220 is applied with a pressure difference caused by different pressures applied to both sides, that is, the negative pressure generated by the discharging of the toothpaste 500 and the atmospheric air pressure formed by the air hole 230. Then, the piston 220 is pushed toward the negative pressure part, so that the piston

220 serves to help the pump 300 effectively pump the toothpaste 500 in the toothpaste storing case 200.

In the toothbrush device of the present invention, the toothpaste is precisely and speedily supplied to the brush of the toothbrush part, the toothpaste is supplied to the center of the brush not to flow down or waste, and the backflow of the toothpaste is prevented by the precise operation of the check valves mounted to the pumps, thereby improving the quality of the toothbrush device.

The toothbrush device includes a path, a connection tube, and first and second check valves, so that the toothpaste is precisely and speedily supplied to the brush of the toothbrush from a toothpaste storing case by a pump, wherein the path is formed in the toothbrush and connected to the pump and the center of a brush, the connection tube connects a connection hole of a push button to the path and has a protrusion part at an end, the first check valve is connected to an end of a pipe in the pump together with a spring and a piston having a rod at a side and to a working element having a securing part, the second check valve has a fixing element formed with a securing part and a fitting part fixed with a rubber plate and positioned in a suction hole of the pump.

A toothbrush device is to resolve the inconvenience caused by the slow and incorrect supply of toothpaste from a toothpaste storing case to a toothbrush.

The foregoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

This application is based on Korean patent application 2004-64407, filed Aug. 16, 2004, the entire contents of which are hereby incorporated by reference, the same as if set forth at length.

What is claimed is:

1. A toothbrush device, comprising:
   a brush, a toothpaste storing case, and a push-button pump disposed between the brush and the toothpaste storing case;
   a first check valve disposed between the toothpaste storing case and the pump, a second check valve disposed between the first check valve and the toothpaste storing case, and a first spring disposed between the first and second check valves;
   wherein the first check valve comprises a second spring and a piston in sequence in a direction away from the pump, and has a working element comprising a rod with movement grooves at a first end thereof and a securing part at a second end thereof;
   wherein the second check valve comprises a fixing element having a fitting part disposed about a central axis at a first end thereof, a securing part disposed at a second end and about an outer periphery thereof, and a rubber plate disposed between the securing part and the toothpaste storing case; and
   wherein the first spring is in contact with the securing part of the first check valve and the securing part of the second check valve.

2. The toothbrush device of claim 1, wherein the pump comprises a push button having a connection hole, and the device further comprises a path between the connection hole and the brush.

3. The toothbrush device of claim 1, the brush comprises a plurality of bristles in contact with a toothbrush head having an opening therein, said opening configured for dispensing toothpaste.

4. The toothbrush device of claim 1, wherein the pump comprises a push button having a connection hole, the brush further comprises a plurality of bristles in contact with a toothbrush head having an opening therein, said opening configured for dispensing toothpaste; and wherein the connection hole is in liquid communication with said opening.

5. The toothbrush device of claim 1, wherein the pump comprises a push button having a connection hole, and the device further comprises a path between the connection hole and the brush;
   wherein a first end of said path connects the connection hole to a connection tube having a protrusion part on an outer periphery thereof;
   and wherein the protrusion part contacts an inner surface of the path.

6. The toothbrush device of claim 5, wherein the protrusion part comprises an o-ring.

7. The toothbrush device of claim 5, wherein the protrusion part is integrally formed with the connection tube.

8. The toothbrush device of claim 5, wherein said protrusion part forms a seal between the outer periphery of the connection tube and the inner surface of the path.

9. The toothbrush device of claim 8, wherein the seal is toothpaste tight sliding seal.

10. The toothbrush device of claim 1, further comprising a pipe disposed between the pump and the first check valve, wherein the rod fits in the pipe via the piston to open or close the movement grooves of the rod in association with an operation of the piston.

11. The toothbrush device of claim 1, wherein the pump further comprises a suction hole; wherein the fixing element and the rubber plate of the second check valve are mounted in the suction hole; and wherein the suction hole of the pump is opened or closed by the rubber plate.

12. The toothbrush device of claim 1, wherein the pump comprises a push button mounted between the brush and the pump, and the push button comprises a first projection that limits the travel of the push button when pushed.

13. The toothbrush device of claim 12, wherein a cap is disposed between the push button and the toothpaste storing case, the cap having a second cavity corresponding to the first projection.

14. The toothbrush device of claim 1, wherein no toothpaste is present in the toothpaste storing case.

15. The toothbrush device of claim 1, wherein toothpaste is present in the toothpaste storing case.

16. A method, comprising contacting the toothbrush device of claim 1 with toothpaste.

17. A method, comprising brushing a subject's teeth with the toothbrush device of claim 1.

* * * * *